(12) United States Patent
Takase et al.

(10) Patent No.: US 6,248,347 B1
(45) Date of Patent: Jun. 19, 2001

(54) CALCIUM ASSIMILATION ACCELERATOR AND CALCIUM-SUPPLEMENTING DIET COMPRISING AND A METHOD FOR ACCELERATING CALCIUM ASSIMILATION

(75) Inventors: Sachiko Takase, Shizuoka; Toshinao Goda, Shimizu; Takehiro Unno, Fuji; Teruo Nakakuki, Mishima, all of (JP)

(73) Assignee: Nihon Shokuhin Kako Co., Ltd., Tokyo (JP)

( * ) Notice: Subject to any disclaimer, the term of this patent is extended or adjusted under 35 U.S.C. 154(b) by 0 days.

(21) Appl. No.: 09/289,728

(22) Filed: Apr. 12, 1999

(30) Foreign Application Priority Data

Apr. 23, 1998 (JP) .................................................. 10-113958

(51) Int. Cl.$^7$ ....................................................... A23K 1/17
(52) U.S. Cl. ............................ 424/442; 424/441; 424/464
(58) Field of Search ................................... 424/464, 442, 424/441

(56) References Cited

U.S. PATENT DOCUMENTS 5,487,989 * 1/1996 Fowler et al. ........................ 435/165

FOREIGN PATENT DOCUMENTS

| 1222779 | 9/1989 | (JP) . |
| 2219584 | 9/1990 | (JP) . |
| 3262460 | 11/1991 | (JP) . |
| 4134031 | 5/1992 | (JP) . |
| 5-67 | 8/1993 | (JP) . |
| 205654 | 7/1994 | (JP) . |
| 6205653 | 7/1994 | (JP) . |

OTHER PUBLICATIONS

Unno, Takehiro, "Industrial Production of Gentiooligosaccharide–Containing Syrups", *Oyo Toshitsu Kagaku*, vol. 42, No. 1, 1995, pp.83–89.

Crowe, Effects of carbohydrates on membrane stability at low water activities AN 1984:98637 CAPLUS abstract, 1984.*

Naito, et al, Bioavailability of calcium affected by luminal and mucosal factors in the small intestine, AN: 1990:75697, CAPLUS, 1990.*

"Effects of Galactooligosaccharides and Fructooligosaccharides on Mineral Utilization in Rats," Susumi Shimura, et al., *Japanese Nutrition and Food Society Journal*, vol. 44, No. 4, pp. 287–291 (1991).

"Maltitol–Induced Increase of Transepithelial Transport of Calcium in Rat Small Intestine," T. Goda, et al., *J. Nutr. Sci. Vitaminol.*, vol. 39, 589–595 (1993).

"Maltitol Increases Transepithelial Diffusional Transfer of Calcium in Rat Ileum," K. Kishi, et al., *Life Sciences*, vol. 59, No. 14, pp. 1133–1140 (1996).

"Effect of β–Glucooligosaccharides on the Human Intestinal Microflora," Takehiro Uno, et al., *Denpun Kagaku, Science of Starch*, vol. 40, No. 1, pp. 21–27 (1993).

* cited by examiner

*Primary Examiner*—James O. Wilson
(74) *Attorney, Agent, or Firm*—Smith, Gambrell & Russell, LLP.

(57) ABSTRACT

Disclosed are an assimilation accelerator which contains β-glucooligosaccharide as an active ingredient, a calcium-supplementing diet which contains β-glucooligosaccharide and a calcium material, and a method for accelerating calcium assimilation using the calcium assimilation accelerator.

19 Claims, No Drawings

CALCIUM ASSIMILATION ACCELERATOR AND CALCIUM-SUPPLEMENTING DIET COMPRISING AND A METHOD FOR ACCELERATING CALCIUM ASSIMILATION

BACKGROUND OF THE INVENTION

The present invention relates to a calcium assimilation accelerator containing β-glucooligosaccharide as an active ingredient, a calcium-supplementing diet containing it, and a method for accelerating calcium assimilation.

β-Glucooligosaccharide is a compound composed of β-glucoside bonds, and a saccharide obtained by β-1,6 bonding and/or β-1,4 bonding of glucoses. It has been known that since these β-glucbside bonds can not be decomposed by internal enzymes, they can be utilized as a low calorie sugar, and accordingly they can be utilized as additives for various diets or refreshments.

Further, in JP-A-3-262460 filed by the present applicant, it has been found that β-glucooligosaccharide has a growing or proliferation effect on bifidobacteria and lactic-acid bacteria, and an intestinal flora (bacteria flora in intestine) improver comprising β-glucooligosaccharide is disclosed. Furthermore, since β-glucooligosaccharide is rich in moisture retention property, its effects on not only a humectant for foods, but also a crystal inhibitor, a glazing agent, an excipient and the like have been recognized, and it can be utilized for medicines.

On the other hand, as a calcium assimilation accelerator, vitamin D has been well known. Although vitamin D has a calcium assimilation-accelerating effect, vitamin D has a problem that its expression mechanism is influenced by homeostasis by hormones, thereby reducing the effect for assimilating the desired calcium amount.

Further, it has been observed that saccharides such as lactose show a calcium assimilation-accelerating effect. However, galactooligosaccharide and fructooligosaccharide have been reported to have an effect for accelerating the assimilation of minerals ("Japanese Nutrition and Food Society Journal", vol. 44, pp 287–291, 1991) and they have been known as a proliferation promoter of bifidobacteria. Furthermore, JP-A-4-134031 discloses a calcium assimilation accelerator comprising galactooligosaccharide as an active ingredient, JP-A-6-205653 discloses a mineral assimilation accelerator comprising lactulose-oligosaccharide as an active ingredient, JP-A-6-205654 discloses a mineral assimilation accelerator comprising a branched galactooligosaccharide as an active ingredient, and JP-A-5-67 discloses diets containing dietary fibers, calcium and maltitol.

However, there has been a problem that over ingestion of saccharides such as lactose and maltitol bring about symptoms such as diarrhea.

SUMMARY OF THE INVENTION

Accordingly, it is an object of the present invention to provide a calcium assimilation accelerator and a calcium-supplementing diet, which have a calcium assimilation-accelerating effect and hardly bring about the symptom of diarrhea unlike the above saccharides, and a method for accelerating calcium assimilation.

The present inventors have extensively studied on substances for accelerating the assimilation of calcium, and have found that β-glucooligosaccharide having β-glucoside bonds accelerates the calcium-assimilating property. The present inventors have accomplished the present invention based on this discovery.

Namely, the first aspect of the present invention is to provide a calcium assimilation accelerator which comprises β-glucooligosaccharide as an active ingredient.

The second aspect of the present invention is to provide a calcium-supplementing diet which comprises β-glucooligosaccharide and a calcium material.

The third aspect of the present invention is to provide a method for accelerating calcium assimilation, which uses a calcium assimilation accelerator comprising β-glucooligosaccharide as an active ingredient.

The fourth aspect of the present invention is to provide a use of β-glucooligosaccharide for accelerating calcium assimilation.

According to the first to fourth aspects of the present invention, since β-glucooligosaccharide has an effect for accelerating calcium assimilation, medicines and diets having β-glucooligosaccharide incorporated therein are useful for supplementing calcium, whereby adequate amount of calcium can be ingested with a high efficiency. Moreover, although β-glucooligosaccharide is not digested nor assimilated in small intestine, it is decomposed in large intestine by intestinal bacteria, particularly bifido bacteria or lactic-acid bacteria, and a part of the β-glucooligosaccharide is assimilated as organic acids, whereby no diarrhea symptom is caused.

MODE FOR CARRYING OUT THE INVENTION

Hereinafter, the present invention will be described in further detail with reference to preferred embodiments.

With respect to β-glucooligosaccharide as an active ingredient of the calcium assimilation accelerator of the present invention, its preparation method is not particularly limited, and, for example, a method for obtaining it by degradation of polysaccharides composed of β-glucoside bonds such as cellulose, laminarin and psutulan, or a method for obtaining it by utilizing a condensation/glucosyltransfer reaction of β-glucosidase, or the like, may be employed.

Nevertheless, it is preferred to employ a method for producing β-glucooligosaccharide easily with a high yield by utilizing a condensation/glucosyltransfer reaction possessed by β-glucosidase by reacting β-glucosidase produced by microorganisms to glucose and/or β-glucooligosaccharide, as described in detail in JP-A-1-222779 and JP-A-2-219584 proposed by the present inventors.

This preparation method will be briefly explained in the following. As the β-glucosidase, ones produced by various microorganisms may be used. For example, it is preferred to employ enzymes produced by microorganisms, for example, flamentous fungi such as *Trichoderma viride, Trichoderma reesei, Trichoderma konignii, Aspergillus niger* and *Penicillium frequentans*; wood-decaying fungi such as *Polypolus tulipiferae, Chrysosporium lignorum* and *Shizophyllum commune*; and bacteria such as *Psuedomonas fluorescens* var.*cellulosa, Cellulomonasuda, Clostridium thermocellum* and *Ruminococcus albus*. These microorganisms are well known and easily available to prepare the enzymes.

Further, as a substrate, D-glucose and/or β-glucooligosaccharide is used. Here, the β-glucooligosaccharide as the substrate means cellobiose, β-glucooligosaccharide, or ones having higher degree of polymerization such as gentiooligosaccharide. When the β-glucooligosaccharide is used as the substrate, it is possible to obtain β-glucooligosaccharide with a higher degree of polymerization by this enzyme reaction. It is particularly preferred to use glucose as the substrate.

When β-glucosidase is reacted to glucose and/or β-glucooligosaccharide, various β-glucooligosaccharides such as cellobiose, gentiobiose, 4-O-β-D-gentiooligosyl-D-glucosce and 6-O-β-D-gentiooligosyl-D-glucose, are obtained. Here, 4-O-β-D-gentiooligosyl-D-glucose means 4-O-β-D-gentiobiosyl-D-glucose, 4-O-β-D-gentiotriosyl-D-glucose or ones having a higher degree of polymerization. Further, 6-O-β-D-gentiooligosyl-D-glucose means 6-O-β-D-gentiobiosyl-D-glucose (gentiotriose), 6-O-β-D-gentiotriosyl-D-glucose (gentiotetraose) or ones having a higher degree of polymerization.

In the present invention, as the β-glucooligosaccharides, it is preferred to use cellobiose, sophorose, laminaribiose, gentiobiose and β-D-gentiooligosyl-D-glucose alone or as a mixture of an appropriate combination.

The calcium-supplementing diet of the present invention contains β-glucooligosaccharide and a calcium material. The calcium material is not particularly limited so far as it is a natural matter or a food additive useful for foods. However, it is preferred to use calcium citrate, calcium carbonate, calcium lactate, tribasic calcium phosphate, calciumhydrogen phosphate, dihydrogen calcium phosphate, calcium chloride, calcined bone calcium, uncalcined calcium, calcined shell calcium and calcined eggshell calcium, alone or as a mixture of an appropriate combination.

The calcium assimilation accelerator of the present invention can be used for the following diets and luxury foods.

Various seasonings such as soy sauce, mirin (sweet cooking sake), mayonnaise, dressing, vinegar, stock of Chinese foods, soup for tempura, sauce, ketchup, sauce for grilled meat, curry roux, stew stock, soup stock, broth stock, composite seasonings and soybean paste; various Japanese confectioneries such as senbei (rice cracker), arare (cubic rice cracker), rice cakes, manju (Japanese bun), uirou (sweet rice jelly), bean jams, yokan (sweetened and jellied bean paste, jelly, kastera (sponge cake) and amedama (candy); various confectioneries such as bread, biscuit, cracker, pie, pudding, butter cream, cream puff, sponge cake, doughnut, chocolate, chewing gum, caramel and hard candy; ices such as ice cream and sherbet; syrups such as fruits pickled with syrup and koori-mitsu; pastes such as flour paste, peanut paste and fruit paste; processed products of fruits such as jam, marmalade, ones pickled with syrup and sweetmeat; pickled vegetables such as fukujin-zuke (sliced and pickled vegetables), senmai-zuke and pickled shallot; livestock products such as ham and sausage; fish meat products such as kamaboko (steamed fish-paste) and chikuwa (steamed fish-paste tube); various delicacies and tukuda-ni (shellfish boiled in sweetened soy sauce); alcohol liquors such as beer, liqueur and sake; cooling beverages such as coffee, cocoa, juice, carbonated beverage, stamina drink, lactic acid drink and lactic acid bacteria drink; instant diets such as instant juice and instant coffee.

With respect to the amounts of β-glucooligosaccharide and calcium material in the calcium-supplementing diet of the present invention, the β-glucooligosaccharide is contained in an amount of preferably from 0.1 to 50 wt %, further preferably from 0.5 to 25 wt %, most preferably from 0.5 to 15 wt %; and the calcium material is contained in an amount of preferably from 0.005 to 2.5 wt %, further preferably from 0.05 to 2.0 wt %, most preferably from 0.1 to 1.0 wt %.

If the amount of the β-glucooligosaccharide is less than 0.1 wt %, the desired calcium assimilation-accelerating effect is hardly obtained, and if exceeds 50 wt %, its specific bitterness tends to damage the flavor and tastiness of diets, such being undesirable.

Further, if the amount of the calcium material is less than 0.005 wt %, the desired calcium supplementing effect by ingestion of diet tends to be poor, and if exceeds 2.5 wt %, it exceeds the standard required amount of calcium and a harsh or acrid taste due to calcium is felt, such being undesirable.

Then, although the expression mechanism of the calcium assimilation-accelerating effect of the present invention is not yetclearly known, it is believed that by drinking or eating the calcium assimilation accelerator of the present invention, spaces between cells of intestine, i.e. a so-called tight junction, is opened, whereby calcium is taken in the body by passive diffusion. This mechanism is believed to be similar to the mechanism of maltitol (T. Godaelal. J. Nutr. Sci. Vitaminol., 39, 589–595 (1993), K. Kishi et al., Life Sci., 59, 1133–1140 (1996)). Further, taking the expression mechanism of the calcium assimilation accelerator of the present invention into consideration, it is believed that assimilation is accelerated for not only calcium, but also minerals such as iron.

Further, as the reason why β-glucooligosaccharide is free from causing the diarrhea symptom as the effect of the present invention, it is believed that the β-glucooligosaccharide is not digested nor assimilated in small intestine, but decomposed in large intestine by intestinal bacteria, particularly bifidobacteria or lactic-acid bacteria, and a part thereof is assimilated as organic acids as mentioned above. This feature is described in further detail in JP-A-3-262460 and "Denpun Kagaku" (Science of Starch), vol. 40, 1, pp 21–27, 1993.

As mentioned above, the calcium assimilation accelerator of the present invention may be used generally by adding to the ones orally taken such as medicines, diets, luxury foods and feeds, and their forms are not particularly limited. For example, when used for medicines, any forms of tablets, granules, capsules, liquid agents and the like, may be used.

EXAMPLE 1

A column equipped with a jacket (60° C.), having an inner diameter of 2 cm and a length of 120 cm, was packed with a cationic exchange resin "Dowex99" ($Na^+$ type, manufactured by Dow Chemical Co.), and then a syrup containing β-glucooligosaccharide (trade name: "Gentose #80", manufactured by Nihon Shokuhin Kako K.K.) was loaded thereinto so that the solid content would be from 5 to 7% (w/v) per resin, followed by fractionation at a space velocity of 0.35 (SV, $hr^{-1}$) to obtain a fraction of β-glucodisaccharide (Gentose G2). This operation was repeated 10 times to obtain 100 g of a fraction of β-glucodisaccharide (Gentose G2). In the above description, β-glucodisaccharide means disaccharides composed of β-glucoside bonds, such as cellobiose, sophorose, laminaribiose and gentiobiose.

TEST EXAMPLE 1

An abdominal region of a Wistar type male rat of 400 g in weight was operated under anesthesia by nenbutal, and a tissue (ileum) of 15 cm in length upward from the point which is 10 cm upward from an ileocelal section toward the mouth, was extirpated. Reversed ileum tissues of each 2.5 cm in length, were prepared, and each of them was fixed on a perforated conical polypropylene tube. The serosa side (inside) thereof was filled with 0.3 ml of a standard buffer (140 mM NaCl, 10 mM $KHCO_3$, 0.4 mM $K_2HPO_4$, 2.4 mM $K_2HPO_4$, pH7.4). As a solution at the mucosa side (outside), was used a standard buffer containing 100 mM of gentiobiose, cellobiose, lactose or Gentose G2 obtained in Example 1, and further 10 mM of $CaCl_2$ added. The gentiobiose, cellobiose and lactose used in this example, are commercially available guaranteed reagents. As a solution at the mucosa side (outside) of the control, was used a standard buffer containing only Ca without adding a saccharide.

The solution at the mucosa side was left to stand warm at 37° C., and gases of $95\%O_2/5\%CO_2$ were continually bubbling. Since it was known that the transepithelial Ca-transportation rate becomes constant after 30 minutes, the serosa side solution was changed to a fresh one when 30 minutes passed after ths tissue was immersed in the solution, and then after 30 minutes passed, the serosa side solution was collected. The Ca concentration in the serosa side solution was measured by a method using orthocresolphthalein conplexone (trade name: "Calcium C test", manufactured by Wako Pure Chemical Industries Ltd.). The transepithelial Ca-transportation rate is represented by indicating the Ca amount transported per 1 $cm^2$ of the mucosa surface area for 30 minutes.

These results are indicated in Table 1.

TABLE 1

| Saccharide | Ca-transportation rate (nmol Ca/30 min./cm$^2$) |
|---|---|
| Nil (Control) | 24.2 ± 2.3 |
| Gentiobiose | 50.3 ± 3.2 |
| Cellobiose | 39.8 ± 2.2 |
| Gentose G2 | 45.5 ± 4.8 |
| Lactose | 45.0 ± 2.7 |

Gentiobiose, Cellobiose and Gentose G2 all accelerated the calcium transportation as compared with the control having no saccharide added, and gentiobiose showed a numerical value of about 2.1 times, cellobiose, about 1.6 times and Gentose G2, about 1.9 times, as compared with the control. Particularly, gentiobiose showed a higher transportation rate than lactose.

EXAMPLE 2

A yogurt jelly having the calcium assimilation-accelerating effect improved, wds prepared by a conventional method with the composition as indicated in Table 2 as shown below.

TABLE 2

| Water | 69.4 g |
|---|---|
| Granulated sugar | 26.0 g |
| Gelling agent | 2.2 g |
| Yogurt | 100.0 g |
| Citric acid | 0.2 g |
| Perfume | 0.4 g |
| Fraction of β-glucodisaccharide (Gentose G2) obtained in Example 1 | 1.6 g |
| Calcium citrate | 0.47 g |

EXAMPLE 3

A neri-an (bean jam paste) having the calcium assimilation-accelerating effect improved, was prepared by a conventional method with the composition as indicated in Table 3 as shown below.

TABLE 3

| Tsubushi aka-nama-an (jam made of crushed red bean not yet sweetened with sugar) | 500 g |
|---|---|
| Granulated sugar | 320 g |
| Gentose #80 | 63 g |
| Calcium lactate | 5.7 g |
| Water | 317 g |

EXAMPLE 4

A cocoa cake having the calcium assimilation-accelerating effect improved, was prepared by a conventional method with the composition as indicated in Table 4 as shown below.

TABLE 4

| Whole egg | 650 g |
|---|---|
| White refined sugar | 256 g |
| Gentose #80 | 86 g |
| Uncalcined calcium | 11 g |
| Weak flour | 300 g |
| Cocoa | 20 g |
| Baking powder | 15 g |
| Salt-free margarine | 100 g |
| Powdered coffee | 10 g |
| Water | 10 g |

EXAMPLE 5

A cocoa-flavored cookie having the calcium assimilation-accelerating effect improved, was prepared by a conventional method with the composition as indicated in Table 5 as shown below.

TABLE 5

| White of egg | 7.5 g |
|---|---|
| Yolk of egg | 14.5 g |
| White refined sugar | 40.0 g |
| Gentose #80 | 14.0 g |
| Weak flour | 100.0 g |
| Cocoa | 10.0 g |
| Calcium lactate | 0.3 g |
| Butter | 70.0 g |

EXAMPLE 6

A pumpkin soup having the calcium assimilation-accelerating effect improved, was prepared by a conventional method with the composition as indicated in Table 6 as shown below.

TABLE 6

| Pumpkin soup | 100.0 g |
|---|---|
| Consomme | 1.8 g |
| Salt | 1.5 g |
| Fraction of β-glucodisaccharide (Gentose G2) obtained in Example 1 | 0.3 g |
| Calcium lactate | 3.3 g |
| Water | 322.0 g |

As mentioned above, according to the present invention, it is possible to impart a calcium assimilation-accelerating effect by using β-glucooligosaccharide. Medicines and diets having β-glucooligosaccharide incorporated, are useful for supplementing calcium, by which adequate amount of calcium can be ingested with a high efficiency, and besides, they do not bring about a symptom of diarrhea.

What is claimed is:

1. A calcium assimilation accelerator composition comprising calcium and a β-glucooligosaccharide selected from the group consisting of gentiobiose, sophorose, laminaribiose, β-D-gentiooligosyl-D-glucose and mixtures thereof, as an active ingredient.

2. The calcium assimilation accelerator composition according to claim 1, wherein a β-glucooligosaccharide is gentiobiose.

3. A calciun-supplementing diet composition comprising a β-glucooligosaccharide selected from the group consisting of gentiobiose, sophorose, laminaribiose, β-D-gentiooligosyl-D-glucose and mixtures thereof, and calcium.

4. The calcium-supplementing diet composition according to claim 3, wherein a β-glucooligosaccharide is gentiobiose.

5. The calcium-supplementing diet composition according to claim 3, wherein the calcium is at least one material selected from the group consisting of calcium citrate, calcium carbonate, calcium lactate, tribasic calcium phosphate, calcium hydrogen phosphate, dihydrogen calcium phosphate, calcium chloride, calcined bone calcium, uncalcined calcium, calcined shell calcium and calcined eggshell calcium.

6. The calcium supplementing diet composition according to claim 3, wherein the β-glucooligosaccharide is contained in an amount of from 0.1 to 50 wt % and the calcium is contained in an amount of from 0.005 to 2.5 wt %.

7. A method for accelerating calcium assimilation in the intestine, comprising administering a calcium assimilation accelerator composition comprising a β-glucooligosaccbaiide selected from the group consisting of gentiobiose, sophorose, laminaribiose, β-D-gentiooligosyl-D-glucose and mixtures thereof, as an active ingredient and calcium.

8. The method for accelerating calcium assimilation according to claim 7, wherein a β-glucooligosaccharide is gentiobiose.

9. A food composition comprising the calcium assimilation accelerator composition of claim 1, in a food product.

10. The food composition according to claim 9, wherein the food is a seasoning, confectionery, fruit, vegetable, fish, beverage or livestock product.

11. The calcium-supplementing diet composition according to claim 3, in the form of a tablet, granule, capsule or liquid.

12. A method for accelerating calcium assimilation, in the intestine of a patient in need thereof, comprising administering an effect amount of the calcium-supplementing diet composition of claim 3.

13. A method for accelerating calcium assimilation, in the intestine of a patient in need thereof, comprising administering an effective amount of a β-glucooligosaccharide selected from the group consisting of gentiobiose, sophorose, laminaribiose, β-D-gentiooligosyl-D-glucose and mixtures thereof in the presence of a calcium material.

14. The calcium supplementing diet composition according to claim 3, wherein the β-glucooligosaccharide is contained in an amount of from 0.1 to 50 wt %.

15. The calcium supplementing diet composition according to claim 3, wherein the β-glucooligosaccharide is contained in an amount of from 0.5 to 25 wt %.

16. The calcium supplementing diet composition according to claim 3, wherein the β-glucooligosaccharide is contained in an amount of from 0.5 to 15 wt %.

17. The calcium supplementing diet composition according to claim 3, wherein the calcium is contained in an amount of from 0.005 to 2.5 wt %.

18. The calcium supplementing diet composition according to claim 3, wherein the calcium is contained in an amount of from 0.05 to 2.0 wt %.

19. The calcium supplementing diet composition according to claim 3, wherein the calciun is contained in an amount of from 0.1 to 1.0 wt %.

* * * * *